United States Patent [19]

Illig et al.

[11] Patent Number: 5,012,000

[45] Date of Patent: Apr. 30, 1991

[54] TOTAL SYNTHESIS OF CHIRAL 2-AMINO-1,3-DIOLS

[75] Inventors: Carl R. Illig; Alexander L. Weis, both of Rochester, N.Y.

[73] Assignee: Eastman Kodak Company, Rochester, N.Y.

[21] Appl. No.: 428,799

[22] Filed: Oct. 30, 1989

[51] Int. Cl.$^5$ ............................................ C07C 209/42
[52] U.S. Cl. ................................. 564/489; 548/243; 552/10; 564/487; 564/507; 564/360
[58] Field of Search ........................ 548/243; 552/10; 564/487, 489, 507, 360

[56] References Cited

PUBLICATIONS

D. A. Evans, J. V. Nelson and T. R. Taber; Top. Stereochem., 13, 1(1982).
"A Practical and Enantioselective Synthesis of Glycoshingolipids and Related Compounds. Total Synthesis of Globotriaosylceramide (Gb$_3$)" by K. C. Nicolaou et al.
"The Total Synthesis Sphingosine", J. Am. Chem. Soc., vol. 80, pp. 1194, 2170, (1958).
"A Steroselective Synthesis of Sphingosine, A Protein Kinase C Inhibitor", Tetrahedron Letters, vol. 29, No. 25, pp. 3037-3040, (1988).
"Synthesis of D-Eyrthrosphingosines", Tetrahedron Letters, vol. 27, p. 481, (1986).
"Synthesis of D-Erythro-1-Deoxydihydroceramide-1-Sulfonic Acid", Tetrahedron Letters, vol. 29, p. 1185, (1988).
M. Schlosser and K. F. Christmann, Ann Fur Chemie, vol. 708, p. 1, et seq., (1967).
"Synthesis of Erythrosphingosines Via Their Azido Derivatives", Liebigs Ann. Ch., pp. 663-667, (1988).
"Asymmetric Synthesis of Anti-B-Hydroxy-alpha-Amino Acids", Tetrahedron Letters, vol. 28, pp. 39-42, (1987).
"Asymmetric Glycine Enolate Aldol Reactions: Synthesis of Cyclosporine's Unusual Amino Acids", J. Am. Chem. Soc., vol. 18, pp. 6757-6761, (1986).
"Metal-Assisted Aldol Condensation of Chiral alpha-Halogenated Chiral Epoxide Synthesis", J. Am. Chem. Soc., vol. 108, pp. 4595-4602, (1986).
"Propane-1,3-dithiol: A Selective Reagent for the Efficient Reduction of Alkyl and Aryl Azides to Amines", Tetrahedron Letters, No. 39, pp. 3633-3634, (1978).
"Sodium Borohydride Reactions under Phase-Transfer Conditions: Reduction of Azides to Amines", J. Org. Chem., 47, 4327, (1982).
Y. Ito, M. Sawayara and T. Hayashi, Tetrahedron Letters, 29, 239, (1988).
D. A. Evans, J. V. Nelson, and T. R. Taber, Top. Sterochem., 13, 1(1982).
"A Practical and Enantioselective Synthesis of Glycoshingolipids and Related Compounds. Total Synthesis of Globotriaosylceramide (Gb$_3$)", by K. C. Nicolaou et al.

*Primary Examiner*—Richard L. Raymond
*Attorney, Agent, or Firm*—Betty Joy Deaton

[57] ABSTRACT

A method for the preparation of chiral 2-amino-1,3-diols is disclosed. The method involves four steps including performance of an aldol condensation with a chiral oxazolidinone on an aldehyde, treating the aldol condensation product with an alkali metal azide, treating the product with a borohydride reagent and reducing the azide to an amine.

3 Claims, No Drawings

TOTAL SYNTHESIS OF CHIRAL 2-AMINO-1,3-DIOLS

FIELD OF THE INVENTION

This invention relates to a process for the preparation of chiral 2-amino 1,3-diols.

CROSS-REFERENCE TO RELATED APPLICATION

This application is related to U.S. Ser. No. 428,800, filed on even date herewith and entitled "Oxazolidinone Aldol Adduct".

BACKGROUND OF THE INVENTION

Glycosphingolipids and gangliosides are of crucial importance as major membrane constituents of the cell, the majority of which are located at the outer leaflet of the plasma membrane. Recent investigations have demonstrated that glycosphingolipids on cell surfaces are one important way in which nature expresses its individuality.

Sphingosine is one of the more important 2-amino 1,5 diols. Sphingosine (or sphingenine) is a ubiquitous membrane component of the natural glycolipids: cerebrosides, sphingomyelins and gangliosides as described in *Sphingolipid Biochemistry*, Plenum Press, N.Y., N.Y.(1983)by J. N. Kanfer and S. Hakomori. This long chain aminoalcohol and its metabolites play important roles in a variety of biological events.

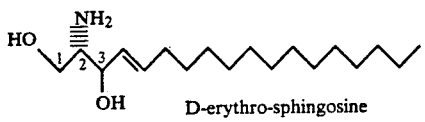

D-erythro-sphingosine

As the lipophilic fragment of glycolipids, sphingosine and its fatty acid derivative ceramide act as an anchor in the phospholipid bilayer. The nature of the lipid and its interaction with the phospholipid bilayer directly influence the manner in which the hydrophilic carbohydrate moiety is presented to the extracellular environment. On the other hand, the stereo specificity of membrane organization as well as the rigidity of the bilayer depends upon the composition of and interaction between the various lipid components.

Glycosphingolipids have numerous extracellular roles. For example, they serve as specific markers of the cells, particularly those forming blood group antigens, tumor cell markers, cell adhesion organ specific markers and growth regulators. They have been also implicated as receptors for toxins, hormones and interferons.

A prominent intracellular regulatory function of sphingosine and its derivatives has been shown. It has also been shown that sphingosine and lysosphingolipids, as components of complex membrane lipids, serve as natural endogenous inhibitors of protein kinase C. The latter has been shown to play a central role in signal transduction for those receptors that function via the phospholipid-dependent second messenger system, modulating cell growth and differentiation.

More recently, dermatological studies on mice have shown that sphingosine inhibits all of the protein kinase C-mediated responses including inflammation, hyperplasia and induction of ornithine decarboxylase activity suggesting a therapeutic application in inflammatory skin diseases.

The complete biological and pharmacological function of sphingosine still remains to be elucidated. Therefore, the development of an efficient stereoselective route to this material and its diastereomers on a multigram scale is still an important synthetic goal.

The important structural features of natural D-(+)-erythro-sphingosine include the absolute configuration at the two chiral centers of this aminodiol (2S, 3R) and the trans geometry of the double bond. Various syntheses of racemic sphingosine have appeared in the literature following the pioneering total synthesis described by Shapiro, et al in "The Total Synthesis of Sphingosine", *J. Am. Chem. Soc.*, Vol. 80, pages 1194, 2170 (1958).

Over the past decade, a number of asymmetric syntheses of sphingosine were published using various synthetic strategies and chiral starting materials. The oldest and perhaps easiest preparation of crude D-sphingosine involves the hydrolysis of the natural sphingolipids. However, the main drawbacks of this procedure are the great expense of the starting materials and the tedious purification of the sphingosine (sphingenine) from dihydrosphingosine (sphinganine) and other impurities. These same drawbacks also apply to chiral resolution techniques using racemic sphingosine.

The presently known synthetic methods for preparation of chiral D-erythro-sphingosine can be ultimately divided into three major categories:

1. Methods utilizing Wittig olefination for preparation of the trans-double bond from configurationally labile 4-carbon α-hydroxyaldehydes. Several chiral α-substituted butyraldehyde derivatives were used in this method which were usually obtained from chiral carbohydrate precursors: D-mannose, D-glucose, D-galactose and D-xylose.

2. Methods which employ optically active α-amino-α,62 -ynone chemistry, preparation of which is based on the 3-carbon backbone of serine and utilizing the (2S)-stereochemistry of L-serine as a chiral precursor to build up the chiral center at carbon 3 described by D. Liotta et al in "A Stereoselective Synthesis of Sphingosine, A Protein Kinase C Inhibitor", *Tetrahedron Letters*, Vol. 29, No. 25, pages 3037-3040 (1988).

3. There are various other miscellaneous procedures described in the art. Of the miscellaneous procedures which are not unreasonably complex, there are two methods used to introduce the olefin:
   (a) Direct stereoselective Wittig olefination.
   (b) Wittig olefination employing the Schlosser modification.

The former method represents the most attractive procedure for introduction of the trans-olefinic bond as exemplified by the salt-mediated method of Schmidt and co-workers in "Synthesis of D-Erythro-sphingosines", *Tetrahedron Lett.*, Vol. 27, page 481 (1986). However, we and other investigators have been unable to reproduce the reported yield and high stereoselection to give "practically exclusively" the trans-alkene product. See "Synthesis of D-Erythro-1-Deoxydihydroceramide-1-Sulfonic Acid" by K. Ohashi, et al, *Tetrahedron Letters*, Vol 29, page 1185 (1988). As a result, several groups have pursued a photochemical cis/trans isomerization with further separation of the isomers, or the Schlosser modification of the Wittig olefination reaction as disclosed in the following reference: M. Schlosser and K. F. Christmann, Ann. Für Chemie, Vol. 708, Page 1(1967).

One of the three most efficient methods of synthesizing sphingosine to date is described by D. Liotta, et al in "A Stereoselective Synthesis of Sphingosine" supra, hereinafter referred to as the "Liotta" reference. The Liotta process involves eight (8) steps starting from the chiral precursor, L-serine, and has an overall yield of approximately 27%. The disadvantages of this process are the great expense of time and money and inefficiency involved in carrying out an eight step process as compared to a process with a lesser number of steps and the inclusion of some racemic yield.

The second of the three most efficient methods of synthesizing sphingosine is described by H. Radunz, et al in "An Efficient and Stereoselective Synthesis of D-erythrosphingosine", supra, hereinafter referred to as the "Radunz" reference. The "Radunz" reference describes a process almost identical to the one described in the Liotta reference. However, it involves seven (7) steps starting from L-serine and has an overall yield of approximately 12-14%.

The third of the three most efficient methods of synthesizing sphingosine is described by P. Zimmermann and R. R. Schmidt in "Synthesis of Erythro-sphingosines Via Their Azido Derivatives", *Liebigs Ann, Chem.*, pages 663-667 (1988). This method begins with chiral carbohydrate precursors, namely D-galactose(or D-xylose). This procedure involves a total of six (6) steps. The overall yield is only 16%.

Further, the reduction of the azide to amine requires the use of hydrogen sulfide which is known to be inherently dangerous.

Therefore, prior to this invention, there has been a need for a process for the preparation of chiral 2-amino-1,3-diols which combines the advantages of less expense, exclusively chiral product, good overall yield, and safety of reagents.

To further understand the nature of this invention, a reaction scheme is provided hereinbelow:

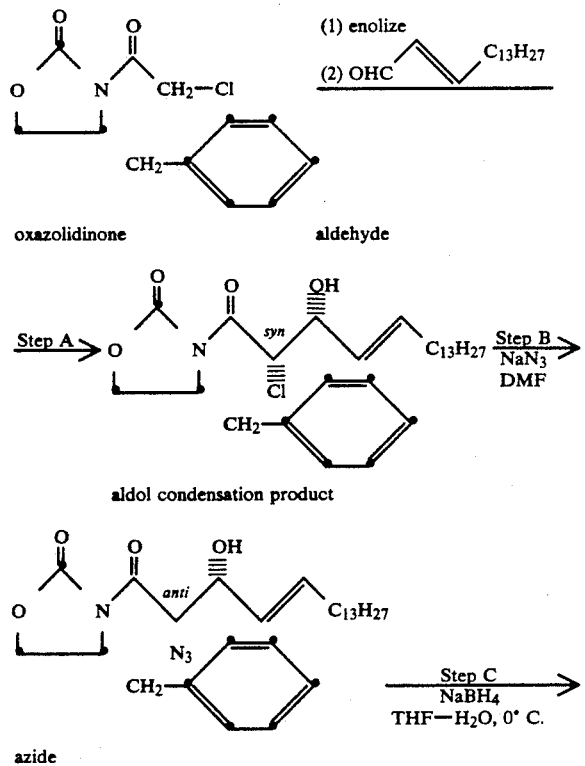

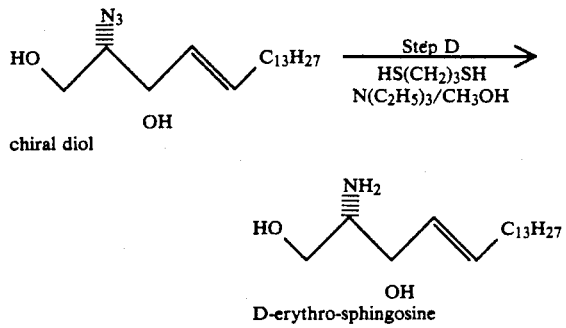

The oxazolidinone aldol adduct formed in Step A is more fully described by Alexander L. Weiss and Carl L. Illig in commonly-owned U.S. Ser. No. 428,800 filed on even date herewith and entitled "Oxazolidinone Aldol Adduct".

SUMMARY OF THE INVENTION

We have developed a process for the preparation of chiral 2-amino 1,3-diols that is effective in solving the above noted problems.

More specifically, in accordance with one aspect of the invention, there is provided a process for the preparation of chiral 2-amino 1,3-diols comprising the steps of:

A. Performing an aldol condensation with a 3-haloacetylated chiral oxazolidinone with an aldehyde using conditions which preserve the chirality of the resulting aldol condensation product;

B. Treating the aldol condensation product with an alkali metal azide;

C. Treating the product of step B with a borohydride reagent to produce a chiral 2-azido 1,3--diol product; and D. Reducing the azide of step C to an amine to produce the chiral 2-amino 1,3-diol product.

In accord with another aspect of the invention, there is provided a process for the preparation of a chiral 3-alkenyl 2-amino-1,3-diol comprising the steps of:

A. Performing an aldol condensation with a 3-haloacetyl-4-substituted chiral oxazolidinone with an α,β-unsaturated aldehyde using a dialkylboron trifluoromethanesulfonate;

B. Treating the aldol condensation product with an alkali metal azide;

C. Treating the product of step B with a borohydride reagent producing a chiral 3-alkenyl 2-azido-1,3-diol; and D. Reducing the azide of step C to an amine to produce the chiral 3-alkenyl-2-amino-1,3-diol.

In a preferred embodiment, D-erythro-sphingosine is the 3-alkenyl-2-amino-1,3-diol that is produced.

In accord with yet another aspect of the invention, there is provided a process for the preparation of D-erythro-sphingosine comprising the steps of:

A. Performing an aldol condensation with 3-haloacetyl-4-substituted chiral oxazolidinone with the trans α,β-unsaturated aldehyde using a dialkylboron trifluoromethanesulfonate.

B. Treating the aldol condensation product with an alkali metal azide.

C. Treating the product of step B with borohydride reagent producing a 2-azido-1,3-diol.

D. Reducing the azide of step C to an amine to produce D-erythro-sphingosine.

It is an advantageous feature of the invention that the process involves only four steps resulting in less expense and time required.

It is another advantageous feature of the invention that it produces exclusively chiral product.

It is yet another advantageous feature of the invention that it produces an overall yield of approximately 30% which is greater than the most efficient methods known in the art.

It is a further advantageous feature of the invention that the chiral oxazolidinone, the chirality inducer, can be recovered and reused thus reducing cost.

Safety of the reagents used in the conversion of the azide to the amine is also an important feature.

It is also an advantageous feature of the invention that an intermediate is formed in the first step of the process which may be used for purposes other than producing 2-amino-1,3-diols, including preparation of 2-halo- and 2-azido 1,3-diols.

Advantageous features other than those noted hereinabove will become apparent upon reference to the following Description of Preferred Embodiments.

DESCRIPTION OF THE PREFERRED EMBODIMENTS

The method of the present invention is useful for the preparation of chiral 2-amino-1,3-diols comprising four steps as follows:

A. Performing an aldol condensation of a 3-haloacetylated chiral oxazolidinone with an aldehyde using conditions which preserve the chirality of the resulting aldol condensation product.

This 3-haloacetylated chiral oxazolidinone is prepared by the haloacetylation of commercially available (S)-4-benzyl-2-oxazolidinone with haloacetyl halide or haloacetic anhydride. The halogen becomes the leaving group, X, and the preferred halogen is bromine which produces greater yields. However, chlorine, fluorine and iodine can also be used.

In this step, an intermediate is formed which has the following formula:

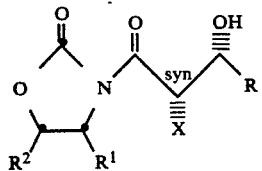

wherein R is alkyl having 6 or more carbons or aryl, $R^1$ is alkyl or aryl, $R^2$ is alkyl, aryl or hydrogen, and X is a halogen atom or an azide. R can be ethyl, propyl, isopropyl, butyl, hexyl, nonyl, hexadecyl, vinyl, propenyl, decenyl, pentadecenyl, phenyl, naphthyl, anthryl, benzyl, phenethyl, tolyl, xylyl, etc.; $R^1$ is alkyl or aryl; $R^1$ can be methyl, propyl, isopropyl, t-butyl, hexyl, isononyl, phenyl, benzyl, phenethyl, etc.; $R^2$ can be methyl, propyl, isopropyl, t-butyl, hexyl, isononyl, phenyl, benzyl, phenethyl, etc.; and X is a halogen atom such as chlorine, bromine, iodine, fluorine, or an azide group.

An example of the use of a chiral 3-haloacetyl-oxazolidinone to make amino acids is disclosed by D. A. Evans, E. B. Sjogren, A. E. Weber and R. E. Conn in "Asymmetric Synthesis of Anti-β-Hydroxy-α-Amino Acids," Tetrahedron Letters, Volume 28, pages 39–42 (1987).

An example of the use of a chiral 3-chloroacetyl oxazolidinone to make other derivatives which are in turn used to make amino acids is disclosed by D. A. Evans and Ann E. Weber in "Asymmetric Glycine Enolate Aldol Reactions: Synthesis of Cyclosporine's Unusual Amino Acids, MeBmt," J. Am. Chem. Soc , Volume 108, pages 6757–6761(1986).

Although any aldehyde can be used, an alkene aldehyde is preferable in order to make sphingosine. Examples of alkene aldehydes are trans-2-hexadecenal (trans-hexadec-2-en-1-al) and crotonaldehyde. Examples of useful saturated aldehydes used to make 2-amino-1-3-diols are listed in "Metal-Assisted Aldol Condensation of Chiral alpha-Halogenated Chiral Epoxide Synthesis," J. Am. Chem. Soc., Vol. 108, pages 4595–4602(1986).

Generally, proportions of reagents can vary over a wide range It is preferred to use greater than one equivalent of the 3-haloacetylated oxazolidinone relative to the aldehyde(1.0–1.5 equivalency).

Conditions which preserve the chirality, i.e., syn-stereochemistry, of the resulting aldol condensation product include use of a tin trifluoromethanesulfonate, or a boron trifluoromethanesulfonate and use of a mild peroxide solution to oxidize the boron such as 30% hydrogen peroxide solution. The use of dibutylboron trifluoromethanesulfonate is preferred. This step is critical in that it must preserve the chiral structure in the resulting aldol condensation product. It is also necessary to avoid strongly basic or acidic reagents or conditions as well as temperatures greater than 20 degrees Celsius. These can result in sideproducts including products resulting from loss of water, isomerization at the chiral center substituted by halogen, epoxide formation from loss of HX, where X is a halogen, or products from a retro-aldol reaction.

B. Treating the aldol condensation product with an alkali metal azide. The preferred alkali metal azide is sodium azide. Alternatively, other azide salts can be used including, but not limited to, lithium azide, potassium azide, cesium azide or a tetraalkylammonium azide. Polar aprotic solvents such as dimethyl sulfoxide are preferred. This step replaces the active halogen with an azido substituent from the sodium azide producing mostly anti product. Isolation of the predominant anti product occurs, i.e., the chiral product.

The amount of azide present must be greater than 1 gram equivalent. The temperature ranges from −78° C. to 100° C. The pH is preferably ≦10 for reactions run in water. Any solvent in which the azide reagent is soluble, but which does not react with the aldol product, can be used. Dimethyl sulfoxide(DMSO) is preferred.

C. The product of step B is treated with borohydride reagent to simultaneously cleave the amide bond, separate the heterocyclic nucleus and convert the amide carbonyl to a hydroxymethyl group thus producing the 2-azido-1,3-diol product. The preferred borohydride reagent is sodium borohydride. Other borohydride reagents could be used including, but not limited to, lithium, potassium or tetraalkylammonium borohydride. The reaction requires greater than two hydride equivalents. An excess of hydride equivalents is generally used. The range of temperature is from −78 degrees Celcius to 110 degrees Celcius. Nearly any solvent unreactive with the borohydride reagent can be used. In the case of sodium borohydride, aqueous solvent mixtures are possible such as water-tetrahydrofuran or water alcohol mixtures.

D. Reducing the azide of step C to an amine to produce the chiral 2-amino 1,3-diol.

There are many different ways of reducing an azide to an amine as illustrated by Bayley, et al in *Propane-1,3-dithiol: A Selective Reagent For The Efficient Reduction of Alkyl and Aryl Azides to Amines*, Tetrahedron Letters No. 39, pp. 3633-3634 (1978), and by Franco Rolla in *Sodium Borohydride Reactions under Phase-Transfer Conditions: Reduction of Azides to Amines*, J. Org. Chem, 47, 4327(1982) and references cited therein.

The preferred method is treatment of the azide with 1,3-dimercaptopropane in basic methanol to produce the 2-amino-1,3-diol. The base and 1,3-dimercaptopropane are generally used in excess. Although methanol works best as a solvent, other polar solvents may be used such as ethanol, N,N-dimethyl-formamide(DMF) or mixtures of pyridine and water. Less polar solvents such as dichloromethane slow the reaction considerably.

The synthesis of chiral 3-alkenyl-2-amino-1,3-diols involves essentially the same steps as the synthesis of chiral 2-amino-1,3-diols as described above with the exception that the aldol condensation of step A is performed specifically with a 3-haloacetyl-4-substituted chiral oxazolidinone and an $\alpha,\beta$-unsaturated aldehyde using a dialkylboron trifluoromethanesulfonate, preferably dibutylboron trifluoromethanesulfonate. Thus, the products of each step are different.

The synthesis of D-erythro-sphingosine involves essentially the same steps as the synthesis of chiral 2-amino-1,3-diols as described above with the exception that the aldol condensation of step A is performed specifically with a 3-haloacetyl-4-substituted chiral oxazolidinone and trans-2-hexadecenal as the $\alpha,\beta$-unsaturated aldehyde using a dialkylboron trifluoromethanesulfonate preferably dibutylboron trifluoromethanesulfonate. Thus, the products of each step are different.

The four step process employs the use of an aldehyde as a starting material. Examples of aldehydes which can be used as the starting material for making 2-amino-1,3-diols include: o-Anisaldehyde, 9-Anthraldehyde, Benzaldehyde, p-Bromobenzaldehyde, p-Butoxybenzaldehyde, o-Chlorobenzaldehyde, 2-Chloro-5-nitrobenzaldehyde, 5-Chloro-2-thiophenecarboxaldehyde, p-Cyanobenzaldehyde, p-Diethylaminobenzaldehyde, 2,5-Dimethoxybenzaldehyde, 3,4-Dimethoxybenzaldehyde, p-Dimethylaminobenzaldehyde, 3,5-Dimethyl-1-phenylpyrazole-4-carboxaldehyde, p-Ethylbenzaldehyde, Furfural, p-Hexylbenzaldehyde, p-Hexyloxybenzaldehyde, 1-Naphthaldehyde, m-Nitrobenzaldehyde, Q-Nitrobenzaldehyde, p-Nitrobenzaldehyde, p-Octylbenzaldehyde, p-Octyloxybenzaldehyde, Piperonal, p-Propylbenzaldehyde, 2-Thiophenecarboxaldehyde and p-Tolualdehyde. The aldehydes are commercially available, for example, from Aldrich Chemical Co., Inc., Sigma Chemical Co., and Eastman Kodak Co. Also, there are many well-known methods of preparing trans-$\alpha,\beta$-unsaturated aldehydes. The aldehyde needed to make sphingosine is not available commercially but can be prepared by the method of Ito(Y. Ito, M. Sawayara and T. Hayashi, *Tetrahedron Letters*, 29, 239(1988). The aldehydes, including trans-2-hexadecenal useful for making sphingosine, can also be more conveniently prepared by the following steps.

A. Preparation of a reagent of the structure:

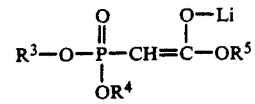

where each $R^3$, $R^4$ and $R^5$ independently is alkyl or aryl such as methyl, ethyl, propyl, benzyl, phenyl, etc., by reaction, i.e., lithiation of a trisubstituted phosphonoacetate with lithium halide in the presence of a base in a dry organic solvent. A trisubstituted phosphonoacetate has the formula:

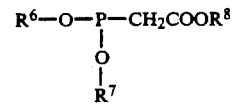

wherein $R^6$, $R^7$ and $R^8$ independently is alkyl or aryl such as methyl, ethyl, propyl, benzyl, phenyl, etc. The solvent used may be any of a number of dry organic solvents including tetrahydrofuran, dioxane and diethyl ether. A dry organic solvent is generally defined as a solvent that has been treated with a drying agent such as $CaCl_2$ or $MgSO_4$ to remove as much water as possible, or distilled from drying agents such as sodium metal, or sodium or calcium hydride. This term is well known in the art. The preferred solvent is tetrahydrofuran. The preferred base is 1,8-diazabicyclo[5.4.0]-undec-7-ene. Alternatively, other bases can be used including any trialkylamine.

Lithium chloride is the preferred lithiating agent. Alternatively, the lithium halide used can be lithium iodide, lithium fluoride or lithium bromide.

B. Condensation of the reagent of step A with tetradecenal is performed to produce the ester of an $\alpha,\beta$-unsaturated carboxylic acid. As stated previously, tetradecanal is the most preferred aldehyde since the product is required to produce sphingosine. However, other aldehydes can be used to produce 2-amino-1,3-diols.

C. Reducing the $\alpha,\beta$-unsaturated carboxylic acid ester to the 2-unsaturated alcohol under conditions such that the double bond is preserved. The conditions refer to strength of the reducing agent. Diisobutylaluminum hydride is preferred. Lithium borohydride or lithium aluminum hydride could also be used.

Conditions are also used which successfully reduce the ester group without also reducing the unsaturated $>C=C<$ and azide groups. Such conditions are well known in the art and are reviewed by J. March in "Advanced Organic Chemistry" 3rd Edition, John Wiley and Sons, New York, N.Y. (1985) beginning at page 1093. (Note particularly Table 5 which provides the reactivity of various functional groups with various metal hydrides and catalytic hydrogenation, and page 1107 relating to the reduction of esters).

D. Oxidizing the 2-unsaturated alcohol to the aldehyde. Pyridinum dichromate is the preferred oxidizing reagent Alternatively, pyridinium, chlorochromate or Moffat-type oxidation reagents including oxalyl chloride-dimethyl sulfoxide, pyridine-sulfur trioxide-dimethylsulfoxide and trifluoroacetic anhydride-dimethylsulfoxide may be used.

EXAMPLE 1

Melting points were determined with a melting point apparatus and are uncorrected. Infrared spectra were recorded on a spectrophotometer. Optical rotations were determined on a polarimeter in a jacketed cell (equipped with a constant temperature bath) at 589 nm (sodium D line) $^1$H NMR spectra were recorded on a spectrometer Chemical shifts are reported in ppm from tetramethylsilane on the $\delta$ scale with residual solvent as the internal standard (chloroform 7.26 ppm). Data are reported as follows: chemical shift, multiplicity (s=singlet, d=doublet, t=triplet, q=quartet, m=multiplet, and br=broad), integration, coupling constant (Hz), and interpretation.

Analytical thin layer chromatography (TLC) was performed using 0.25 mm silica gel plates visualized by UV fluorescence and by an aqueous ceric ammonium molybdate spray followed by heat. Routine liquid (flash) chromatography was performed on 32–63 $\mu$m silica gel with the indicated solvent system. The solvent system used to prepare the column, if different, is reported separately.

When necessary, solvents and reagents were dried prior to use Diethyl ether and tetrahydrofuran were distilled from sodium metal/benzophenone ketyl. Toluene was distilled from sodium metal. Dichloromethane, and triethylamine were distilled from calcium hydride under an argon atmosphere. Nonaqueous titration grade N,N dimethylformamide was stored over activated 4Å molecular sieves under an argon atmosphere Reagent grade pyridine was stored over potassium hydroxide under an inert (argon) atmosphere.

Anhydrous acetonitrile, anhydrous dimethyl sulfoxide, diisobutylaluminum hydride in toluene, and (S)-(−)-4-benzyl-2-oxazolidinone were obtained from Aldrich Chemical Co.

(S)-3-bromoacetyl-4-benzyl-2-oxazolidinone and S-3-chloroacetyl-4-benzyl-2-oxazolidinone were prepared by the procedures of A. Abdel-Magid, L. N. Pridgen, D. S. Eggleston, and I. Lantos as described in "*Metal Assisted Aldol Condensation of Chiral α-Halogenated Imide Enolates: A Sterocontrolled Chiral Epoxide Synthesis*", J. Am. Chem. Soc. 108, 4595–4602 (1986).

Anhydrous lithium chloride was prepared by drying the finely powdered salt at 300° C. for 5 h.

Moisture sensitive reactions were carried out under an atmosphere of argon using oven-dried glassware. All solutions were magnetically stirred unless otherwise indicated.

Trans-Ethyl-2-Hexadecenoate

To a solution of 18.8 g (0.443 mol) of anhydrous lithium chloride in 1200 mL of dry acetonitrile and 600 mL of dry tetrahydrofuran was added 99.3 g (0.369 mol) of triethyl phosphonoacetate followed by 55.2 mL (0.369 mol) of 1,8-diazabicyclo[5.4.0]undec- 7-ene. After 5 min at 25° C., 98.0 g (0.369 mol based on 80% purity) of technical grade tetradecanal in 600 mL of tetrahydrofuran was added. After stirring for 1.5 h, the mixture was poured into 16 L of water and extracted with 3×2.5 L of technical grade diethyl ether. The combined organic extracts were washed with 4 L saturated aqueous sodium bisulfite to remove unreacted aldehyde, then with 2 L of brine and dried over sodium sulfate. The solution was concentrated to a milky oil and placed under vacuum (0.5 torr/4 h) to afford 140 g of an oily white suspension. The mixture was fractionally distilled collecting a small amount of tetradecanal (104–107° C./0.45 torr then 128–137° C./0.25 torr) followed by 98.1 g (94%) of pure trans-ethyl 2-hexadecenoate (137–142° C./0.25 torr) as a colorless mobile oil.

IR (thin film) 2920, 2850, 1725, 1465, 1265, 1175, 1045 cm$^{-1}$;$^1$H NMR (CDCl$_3$, 300 MHz) $\delta$. 7.00 (dt, 1, J=15.5, 6.8 Hz, CH$_2$CH=), 5.84 (dt, 1 J=15.5, 1.2 Hz, COCH=), 4.21 (dd, 2, $\overline{J}$=14.2, 7.2 Hz, CH$_2$O), 2.23 (qd, 2, J=6.9, 1.2 Hz, CH$_2$CH=), 1.49 (t, 2, J=7 Hz, CH$_2$CH$_2$CH$_3$), 1.3 (m, $\overline{20}$, CH$_2$CH$_2$CH$_2$), 0.92 (t, 3, J=7 Hz, C$\overline{H}_2$CH$_2$CH$_3$). R$_f$(5% ethyl acetate:hexanes): tetradecanal, 0.29; ester product, 0 31. MS (FD): m/e 282 (M+).

Trans-2-hexadecenol

To a cooled (0° C.) solution of 35.1 g (0.124 mol ) of trans-ethyl 2-hexadecenoate in 100 mL of dry toluene was added 298 mL (0.298 mol) of a 1.0 M solution of diisobutylaluminum hydride in toluene over ca. 6 min. After stirring for 45 min, the mixture was carefully quenched with 20 mL of absolute methanol. The mixture was poured into 1.5 L of 0.5 M sodium potassium tartrate and mechanically stirred vigorously for 5 h. After standing undisturbed for 14 h, the mixture was filtered through diatomaceous earth, referred to hereinafter as Celite, (the Celite is moistened with a solvent and poured onto a filter paper in a Buchner funnel under vacuum to form a pad of the Celite over the paper), the layers separated and the aqueous layer extracted with 100 mL ethyl acetate. The combined organic layers were dried over sodium sulfate and concentrated to afford 29.5 g (99%) of a soft, waxy white solid. This material was used directly in the following reaction.

IR (thin film) 3000–3500, 2920, 2850, 1420, 970 cm$^{-1}$; $^1$H NMR (CDCl$_3$, 300 MHz)$\delta$5.6–5.8 (m,2, CH=CH), 4.11 (d, 2, J=4.9 Hz, CH$_2$OH), 2.04 (q, 2, J=6.4 Hz, CH$_2$CH=), 1.0–1.3 (m, $\overline{22}$, CH$_2$), 0.91 (t, 3, J=7 Hz). R$_f$(15% methanol:dichloromethane): trans-ethyl 2-hexadecenoate, 0.60; trans-2-hexadecenol, 0.17.

Trans2-hexadecenal

To a stirred suspension of 60.6 g (0.161 mol) pyridinium dichromate in 100 mL of dichloromethane was added 25.7 g (0.107 mol) of trans-2-hexadecenol. After 4 h at 25° C., the mixture was filtered (through Celite diatomaceous earth) and the resulting brown solution refiltered through Florisil, an activated magnesium silicate in the form of hard, porous, stable, white granules that are free from dusting sold by Floridin Co. The colorless solution obtained was concentrated in vacuo to 21.8 g (86%) of a white solid. Distillation (90–100° C./0.40–0.45 torr) provided 19.1 g (75%) of pure trans-2-hexadecenal as a white waxy solid. IR (thin film as melt) 2920, 2850, 1695, 1465, 975 cm$^{-1}$; $^1$H NMR (CDCl$_3$, 300 MHz) $\delta$ 9.53 (d, 1, J=6.7 Hz, CHO), 6.88 (overlapping dt. 1, J=15.7, 6.7 Hz, OHCCH=), 1.53 (m, 2CH$_2$CH$_3$), 1.1–1.2 (m, 20, CH$_2$CH$_2$CH$_2$), $\overline{0.90}$ (t, 3, J=7 Hz, CH$_2$CH$_3$). R$_f$ (15% ethyl acetate:hexanes): trans-2-hexadecenol, 0.19 trans-2-hexadecenal, 0.44. MS(FD) m/e 238 (M+).

Aldol Adduct
(S)-4-Benzyl-3-(trans-2-chloro-3-hydroxy-4-octadecenoyl)-2-oxazolidinone from
(S)-4-Benzyl-3-bromoacetyl-2-oxazolidinone To a flame dried flask under argon was added 2.481 g (9.780 mmol) of (S)-3-chloroacetyl-4-benzyl-2-oxazolidinone and the flask was reflushed with argon to exclude all traces of oxygen. 300 mL of dry oxygen free diethyl ether (freshly distilled from sodium/benzophenone ketyl under argon) was added and the resulting solution cooled over 5 min to −35° C. (internal temperature). The freshly distilled oxygen free triethylamine (2.30 mL, 16.5 mmol) was added. Cooling was continued and immediately upon reaching an internal temperature of −50° C. (to prevent crystallization of the dissolved imide), 10.8 mL (10.8 mmol) of a 1.0 M solution of dibutylboron triflate in dichloromethane was added dropwise over 3 min (maintaining the temperature at −50±2° C.). The pale yellow solution was stirred 15 min at −50° C., warmed to 20° C. over ca. 45 min and stirred at 20° C. for 30 min. (Triethylamine hydrotriflate precipitated as a white solid becoming an oil above 0° C.) The solution was recooled to −65° C. (internal temperature) and 1.667 g (6.990 mmol) of trans-2-hexadecenal in 20 mL of dry, oxygen-free diethyl ether was added by cannula. After stirring at −65° C. for 15 min, the solution was warmed to 0° C. over 1.5 h, stirred at 0° C. for 30 min and the cooling bath was removed. Thin layer chromatography analysis during this time indicated the disappearance of all but 5-10% of the starting aldehyde. After stirring an additional 30 min, the internal temperature had reached 20° C. Ethyl acetate (200 mL) was added and the solution washed with 2×150 mL of 0.5 M aqueous sodium bisulfate, 200 mL of brine and dried over anhydrous sodium sulfate. The solution was then concentrated in vacuo to 5.9 g of a pale amber oil which was redissolved in 50 mL of diethyl ether. The 30% hydrogen peroxide (15 mL) was added followed by sufficient absolute ethanol to obtain a homogeneous solution (ca. 50 mL). After stirring at 20° C. for 14 h, the mixture was concentrated in vacuo without warming (bath temperature ≦20° C.) to ca. 20% volume to remove the majority of the solvents. Ethyl acetate:hexane (1:1 200 mL) was added and the solution washed with 100 mL of water, 100 mL of saturated aqueous sodium bicarbonate, brine and dried over anhydrous sodium sulfate. Concentration in vacuo (≦20° C.) afforded 4.7 g of a colorless resin. The mixture was flash chromatographed on 400 g of silica gel eluting with a gradient of 4% ethyl acetate in dichloromethane:hexanes (40:60) to 6% ethyl acetate in dichloromethane:hexanes (60:40) over ca. 4 L. First eluted was 98 mg (5.9%) unreacted trans-2-hexadecenal followed by the unreacted excess imide (mixed with a minor diastereomeric aldol product) followed by 2.082 g (61%) of the desired aldol adduct as a nearly colorless resin (64% based on recovered aldehyde): $[\alpha]_D 20 + 52.7°$ C. (c 1.3, $CH_2Cl_2$); IR (thin film) 3200-3600, 2920, 2850, 1780, 1710, 1390, 1210, 1110, 900 $cm^{-1}$; $^1H$ NMR ($CDCl_3$, 300 MHz) δ 7.2-7.4 (m, 5, Ph), 5.89 (dt, 1, J=15.5, 6.8 Hz, CHC$\underline{H}$=), 5.74 (d, 1, J=5.0 Hz, C$\underline{H}$Cl), 5.55 (dd, 1, J=15.5, 6.6 Hz, $CH_2C\underline{H}$=), 4.72 (m, 1, NC$\underline{H}$), 4.64 (br t, 1, J=5.3 Hz, C$\underline{H}$OH), 4.27 (d, 2, J=7.3 Hz $C\underline{H}_2O$), 3.35 (dd, 1, J=13.4, 3.3 Hz, $C\underline{H}_2Ph$), 2.87 (dd, 1, J=13.4, 9.4 Hz, $C\underline{H}_2Ph$), 2.73 (br s, 1, OH), 2.08 (dd, 2, J=13.8, 6.8 Hz, $C\underline{H}_2CH$=), 1.05-1.25 (m,22, $CH_2$), 0.91 (t, 3, J=6 Hz, $CH_3$). $R_f$(4% ethyl acetate:dichloromethane):trans-2-hexadecenal, 0.66; imide, 0.60; minor aldol diastereomer, 0.53; major aldol diastereomer adduct product, 0.45.

(S)-3-(Trans-2azido-3-hydroxy-4-octadecenoyl)-4-benzyl-2-oxazolidinone from (S)-4-Benzyl-3-(trans-2-chloro-3-hydroxy-4-octadecenoyl)-2--oxazolidinone To 1.21 g (2.46 mmol) of the aldol adduct and 351 mg (5.4 mmol) of sodium azide was added 12.0 mL of dry N,N-dimethylformamide and warmed to 40-45° C. until TLC analysis (25% ethyl acetate:hexanes) indicated that ca. 5% trans-2-hexadecenal (from retroaldol reaction) was present, at which point the displacement was ≧95% complete (3.0-4.5 h). (Monitoring by disappearance of starting aldol adduct was difficult due to its co-elution on TLC with the azide product minor diastereomer.) The mixture was partitioned between 200 mL of ethyl acetate:hexanes (1:1) and 200 mL of water. The aqueous layer was extracted with 50 mL of ethyl acetate:hexanes (1:1) and the combined organic layers washed with 3×100 mL water (emulsions broken by addition of brine), 100 mL of brine and dried over anhydrous sodium sulfate. Concentration in vacuo afforded 1.19 g of a yellow oil which $^1H$ NMR spectral analysis revealed to contain an 86:14 mixture of azide epimers A and B, respectively, along with small amounts (<10%) of products from the retroaldol reaction. Flash chromatography on 150 g silica gel (20% ethyl acetate:hexanes) provided 27.5 mg (4.7%) of trans-2-hexadecenal followed by 0.822 g (67%) of the pure azide product (epimer A) as a colorless oil. Last eluted was 164 mg of a mixture of a minor azide epimer B and 3-azidoacetyl-4-benzyl-2-oxazolidinone (the result of an azide displacement on the retroaldol product 3-chloroacetyl-4-benzyl-2-oxazolidinone) followed by 70 mg of a colorless oil consistent, by $^1H$ NMR, with the pure minor azide diastereomer B. Data for the product, diastereomer A: $[\alpha]_D^{20} + 26.8°$ (c 1.1, $CH_2Cl_2$); IR (thin film) 3250-3600, 2920, 2850, 2110, 1780, 1705, 1390, 1210, 1115, 700 $cm^{-1}$; $^1H$ NMR ($CDCl_3$, 300 MHz) δ 7.1-7.2 (m, 5, Ph), 5.93 (overlapping dt, 1, J=15.4, 6.7 Hz, OC—C$\underline{H}$=), 5.62 (dd, 1, J=15.4, 7.3 Hz, $CH_2C\underline{H}$=), 5.08 (d, 1, J=7.7 Hz, CHN$_3$), 4.73 (m, 1, NC$\underline{H}$), 4.52 (q, 1, J=6.9 Hz, C$\underline{H}$OH), 4.23 (m, 2, $CH_2O$), 3.32 (dd, 1, J=13.5, 3.4 Hz, C$\underline{H}_2Ph$), 2.76 (dd, 1, J=13.5, 9.7 Hz $C\underline{H}_2PH$=), 2.44 (d,1, J=7.0 Hz,OH) 2.10 (q,2,J=6.9 Hz, $C\underline{H}_2CH$=), 1.1-1.5 (m, 22, $CH_2$), 0.88 (t, 3, J=7 Hz, $CH_3$) $R_f$ (25% ethyl acetate:hexanes): starting aldol adduct, 0.20; major azide product epimer A, 0.33; minor azide epimer B, 0.20; trans-2-hexadecenal, 0.90.

Azidodiol

To a cooled (0° C.) solution of 0.430 g (0.862 mmol) of the azide epimer A in 20 mL of tetrahydrofuran:water (2:1) was added 65.1 mg (2.07 mmol) of sodium borohydride in two portions at 30 min intervals. After stirring an additional 15 min, the mixture was carefully quenched by slow addition of 30 mL of 0.5 M aqueous sodium bisulfate. The mixture was extracted with 3×20 mL of dichloromethane and the combined extracts washed with 30 mL of brine and dried over anhydrous sodium sulfate. Concentration in vacuo provided 0.425 g of a pale amber oil. Flash chromatography on 65 g of silica gel (20% ethyl acetate:hexanes) afforded 223 mg (80%) of the azidodiol product as an off-white crystalline solid. Recrystallization from hexanes provided an analytical sample: mp 54.5-55.0° C., $[\alpha]_D^{20}$—34.4° (c 1.1, $CH_2Cl_2$), IR ($CHCl_3$) 3600, 3200-3600, 2920, 2850, 2105, $cm^{-1}$; $^1H$ NMR ($CDCl_3$, 300 MHz) δ 5.84 (dt, 1, J=15.4, 6.6 Hz, HC=), 5.56 (dd, 1, J=15.4, 7.3 Hz, HC=), 3.53 (dd, 1, J=10.5, 5.3Hz CHN3), 2.09 (m, 2, CH2CH=), 1.1–1.4 (m, 22, CH2), 0.89 (t, 3, J—7 Hz, CH3) $R_f$ (50% ethyl acetate:hexanes): azide diastereomer A, 0.90; azidodiol product, 0.43; 4-benzyl-2-oxazolidinone, 0.14. Anal calcd for $C_{18}H_{35}N_3O_2$: C, 66.42; H, 10.84; N, 12.91. Found: C, 66.39; H, 10.50; N, 12.55.

D-erythro-sphingosine

A solution of 0.141 g (0.433 mmol) of the azidodiol, 0.217 mL (2.17 mmol) of 1,3-propanedithiol and 0.302 mL (2.17 mmol) of triethylamine in 3.0 mL of absolute methanol was stirred at 25° C. for 40 h. After concentration in vacuo, the excess dithiol was removed under vacuum (60° C./0.25 torr/4 h) to afford 0.192 g of a white solid. This material was dissolved in a minimum of warm methanol-dichloromethane (1:1) and purified by flash chromatography on 40 g of silica gel (packed in 5% solution of methanol:ammonia (40:1 wt/wt) in dichloromethane and eluted with a 5–10% gradient of the same solvent over 850 mL) to produce 0.118 g (91%) of pure D-erythro-sphingosine as a white solid. An analytical sample was obtained as a white powder by slow evaporation from hexanes: mp 81–82° C. (Lit:83.0–83.5° C., 80–84° C.); $[\alpha_D^{20}+10.1$ (c 1.1, EtOH), IR (CHCl3) 3600, 3200–3600, 2920, 2850 cm$^{-1}$; $^1$H NMR (CDCl3, 300 MHz) δ 5.76 (dt, 1, J=15.4, 6.6 Hz, CHCH=), 5.47 (dd, 1, J=15.4, 7.0 Hz, CH2CH ), 4.05 (t, 1, J=6.0 Hz, CHOH), 3.66 (m, 2, CH2OH), 2.88 (br s, 1, CHNH2), 2.06 (q, 2, J=6.9 Hz, CH2CH=), 1.93 (br s, 4, OH, NH2), 1.1–1.4 (m, 22, CH2), 0.88 (t, 3, J=7 Hz, CH3). $R_f$ (5% methanol:dichloromethane saturated with ammonia):azidodiol, 0.55; sphingosine, 0.27. Exact mass (Fast atom bombardment ionization, thioglycerol), calcd for $C_{18}H_{38}NO_2$ (M+H):300.2902. Found: 300.2911.

D-erythro-sphingosine-triacetate (20)

To a cooled (0° C.) solution of 38.1 mg (0.127 mmol) of D-erythro-sphingosine 1 in 3.0 mL of dichloromethane was added 61.5 μL (0.762 mmol) of pyridine, 72.0 μL (0.762 mmol) of acetic anhydride and 0.78 mg (6.4 μmol) of 4-dimethylaminopyridine. The solution was warmed to 25° C., stirred for 2 h and poured in 30 mL of dichloromethane. The mixture was washed with 40 mL each of saturated aqueous sodium bicarbonate, saturated aqueous cupric sulfate, brine and dried over anhydrous sodium sulfate. Concentration in vacuo yielded 52.3 mg (97%) of nearly pure triacetate as an off-white solid. Recrystallization from hexanes afforded 48.2 mg (89%) of pure triacetate as feathery white crystals, mp 102–103° C. A second recrystallization from diethyl ether:hexanes gave an analytical sample as feathery white crystals, mp 103.0–103.5° C.

(Lit:103° C.,103.5–104.5° C.); $[\alpha]_D^{20}$—13.3° C. (c = 1.0, CHCl3 passed through basic alumina).

(Lit.:$[\alpha]_D^{25}$—12.9° (C 1, CHCl3), $[\alpha]_D^{24}$—12.9° (CHCl3), IR (CHCl3) 3020, 2930, 2860, 1738, 1675, 1510, 1375, 1235 cm$^{-1}$; $^1$H NMR (CDCl3, 300 MHz) δ5.79 (dt, 1, J=15.3, 6.7 Hz, CHCH=), 5.63 (d, 1, J=9.5 Hz, NH), 5.39 (dd, 1, J=15.3, 7.6 Hz, CH2CH=), 5.27 (t, 1, J=6.8, AcOCH), 4.43 (m, 1, NCH), 4.30 (dd, 1, J=11.5, 6.0 Hz, AcOCH2), 4.03 (dd, 1, J=11.5, 3.9 Hz, AcOCH2), 2.07 (s, 3, CH3CO), 2.06 (s, 3, CH3CO), 2.03 (m, 2, CH2CH=), 1.99 (s, 3, CH3CO), 1.2–1.4 (br s, 22, CH3), 0.88 (t, 3, J=7 Hz, CH3). $R_f$ (5% methanol:dichloromethane: D-erythro-sphingosine, 0.03; triacetate product, 0.33. Exact mass (FAB, thioglycerol) calcd. for $C_{24}H_{44}CO_5$ (M+H):426.3219, found: 426.3217.

EXAMPLE 2

Aldol Adduct
(S)-4-Benzyl-3-(trans-2-bromo-3-hydroxy-4-Octadecenoyl)-2-oxazolidinone from (S)-3-Bromoacetyl-4-benzyl-2-oxazolidinone.

To an oven-dried flask under argon in a dry box was added 2.97 g (9.98 mmol) of (S)-3-bromoacetyl-4-benzyl-2-oxazolidinone, and the flask was reflushed with argon to exclude all traces of oxygen. 300 mL of dry oxygen-free diethyl ether (freshly distilled from sodium/benzophenone ketyl under argon) was transferred by cannula into the flask, and the resulting solution cooled over 5 min. to −35° C. (internal temperature). The freshly distilled oxygen-free triethylamine (2.30 mL, 16.5 mmol) was added. Cooling was continued and, upon reaching an internal temperature of −78° C., 10.8 mL (10.8 mmol) of a 1.0 M solution of dibutylboron triflate in dichloromethane was added dropwise over 3 min. the pale yellow solution was stirred 15 min. at −78° C., warmed to 20° C. over ca. 45 min. and stirred at 20° C. for 30 min. (Triethylamine hydrotriflate precipitated as a white solid becoming an oil above 0° C.) The solution was recooled to −65° C. (internal temperature), and 1.67 g (6.99 mmol) of trans-2-hexadecenal in 20 mL of dry, oxygen-free diethyl ether was added by cannula. After stirring at −65° C. for 15 min., the solution was warmed to 0° C. over 0.5 h, stirred at 0° C. for 40 min., and the cooling bath was removed. TLC analysis during this time indicated the disappearance of all of the starting aldehyde. After stirring an additional 30 min., the internal temperature had reached 20° C. Ethyl acetate (200 mL) was added, and the solution was washed with 2×150 mL of 0.5 M aqueous sodium bisulfate and 200 mL of brine.

The solution was then concentrated in vacuo to a pale amber oil which was redissolved in 50 mL of diethyl ether. Hydrogen peroxide (30%, 15 mL) was added followed by sufficient absolute ethanol to obtain a homogeneous solution (ca. 50 mL). After stirring at 20° C. for 14 h, the mixture was concentrated in vacuo without warming (bath temperature ≦20° C.) to ca. 20% volume to remove the majority of the solvents. Ethyl acetate:hexane (1:1, 200 mL) was added and the solution washed with 100 mL of water and 100 mL of saturated aqueous sodium bicarbonate. An emulsion formed which was broken up by addition of 200 mL of brine followed by extraction with 2×500 mL of ethyl acetate:hexane (1:1). The combined extracts were washed with 300mL of brine and dried over anhydrous sodium sulfate. Concentration in vacuo (≦20° C.) afforded 5.2 g of a colorless resin. The mixture was flash chromatographed on 400 g of silica gel eluting with a gradient of 4% ethyl acetate in dichloromethane: hexanes (40:60) to 6% ethyl acetate in dichloromethane:hexanes (60:40) over ca. 4L. First eluted was unreacted excess imide followed by 4.43 g (81%) of the desired aldol product as a nearly colorless resin. This material is somewhat unstable and should be used immediately in the azide displacement reaction.

Mass spectrum (field desorption ionization) m/e=535 (M+), 455 (—HBr).

$^1$H NMR (CDCl3, 300 MHz)δ 7.195–7.374 (m, 5, Ph) 5.891 (dt, 1, J=15.5, 6.6 Hz, CHCH=) 5.677 (d, 1,

J=5.3 Hz, CHBr) 5.487 (dd, 1, J=15.5, 6.6 Hz, CH$_2$CH=), 4.723 (m, 1, NC$\underline{H}$) 4.680 (dt, 1, J=5.3 Hz, CH—$\overline{O}$H) 4.270 (d, 2, J=7.3 Hz, CH$_2$O) 3.295 (dd, 1, J=13.4, 3.3 Hz, CH$_2$Ph), 2.807 (dd, 1, J=13.4, 9.4 Hz, CH$_2$Ph) 2.030 (dd, 2, J=13.8, 6.8 Hz, CH$_2$CH=) 1.24–1.38 (m, 22, CH$_2$) 0.872 (t, 3, J=6 Hz C$\overline{H}$$_3$).

EXAMPLE 3

(S)-3-(Trans-2-azido-3-hydroxy-4-octadecenoyl-4-benzyl-2-oxazolidinone from (S)-4-Benzyl-3-(trans-2-bromo-3-hydroxy-4-octadecenoyl)-2-oxazolidinone.

To 536 mg (1.00 mmol) of bromoaldol compound in 10 mL of dry dimethyl sulfoxide was added 130 mg (2.00 mmol) of sodium azide, and the reaction mixture was stirred at 20° C. After 18 h, the DMSO was evaporated without warming at high vacuum (10$^{-3}$ Torr), and the residue was treated with 120 mL of water and extracted three times with 100 mL of ethyl acetate:hexane, 1:1. The combined organic layer was washed with 50 mL brine and dried over anhydrous sodium sulfate. Concentration in vacuo afforded an oil which, according to the $^1$H NMR spectrum, contained a 9:1 mixture of azide epimers.

Flash chromatography on 80 g of silica gel with 20% ethyl acetate:hexane gave 418 mg (84%) of the pure desired azide epimer as an oil (Rf 0.33, 25% ethyl acetate:hexane). Next eluted was 43 mg (9%) of the minor azide epimer (Ref 0.20). $^1$H NMR spectral data of both products were identical to materials produced from the corresponding chloro derivative ((S)-4-benzyl-3-(trans-2-chloro-3-hydroxy-4-octadecenoy 1)-2-oxazolidinone).

The invention has been described in detail with particular reference to preferred embodiments thereof, but it will be understood that variations and modifications can be effected within the spirit and scope of the invention.

What is claimed is:

1. A process for the preparation of chiral 2-amino-1,3-diols comprising the steps of:
    A. Performing an aldol condensation with a 3-haloacetylated chiral oxazolidinone with an aldehyde using conditions which preserve the chirality of the resulting aldol condensation product;
    B. Treating the aldol condensation product with an alkali metal azide;
    C. Treating the product of step B with a borohydride reagent to produce a chiral 2-azido-1,3-diol product; and
    D. Reducing the azide of step C to an amine to produce the chiral 2-amino-1,3 diol product.

2. A process for the preparation of a chiral 3-alkenyl-2-amino-1,3-diol comprising the steps of:
    A. Performing an aldol condensation with a 3-haloacetyl-4-substituted chiral oxazolidinone with an α,β-unsaturated aldehyde using a dialkylboron trifluoromethanesulfate;
    B. Treating the aldol condensation product with an alkali metal azide;
    C. Treating the product of step B with a borohydride reagent producing a chiral 3-alkenyl-2--azido-1,3-diol;
    D. Reducing the azide of step C to an amine to produce the chiral 3-alkenyl-2-amino-1,3-diol.

3. The process according to claim 1 wherein the oxazolidinone of step A is a 3-haloacetyl-4-substituted chiral oxazolidinone, the aldehyde of step A is trans-2-hexadecenal, and the product of step D is D-erythrosphingosine.

* * * * *